United States Patent [19]

Grollier et al.

[11] 4,323,468
[45] Apr. 6, 1982

[54] MAKE-UP REMOVER COMPOSITION FOR THE FACE AND EYES

[75] Inventors: Jean-Francois Grollier, Paris; Josiane Allec, Pierrefitte, both of France

[73] Assignee: L'Oreal, Paris, France

[21] Appl. No.: 149,115

[22] Filed: May 12, 1980

[30] Foreign Application Priority Data

May 15, 1979 [LU] Luxembourg ............ 081257

[51] Int. Cl.³ .............................. C11D 1/72
[52] U.S. Cl. ...................... 252/174.17; 252/89.1; 252/174.11; 252/522 A; 252/DIG. 5; 424/364

[58] Field of Search ............ 252/174.11, 174.17, 252/89.1, 522, DIG. 5; 424/364

[56] References Cited

U.S. PATENT DOCUMENTS 259,389  6/1882  Henderson ............ 252/140 X

Primary Examiner—Mayer Weinblatt

[57] ABSTRACT

A makeup removal composition comprises an aqueous carrier, a synthetic surface-active agent and an effect amount of an extract of sarsaparilla (*Smilax Species*).

5 Claims, No Drawings

MAKE-UP REMOVER COMPOSITION FOR THE FACE AND EYES

The object of the present invention is a cosmetic composition for the removal of make-up from the face and the eyes, this composition containing, in so far as the cleaning substance is concerned, the combination of a synthetic surface-active agent and an extract of sarsaparilla (*Smilax Species*), a plant belonging to the Liliaceae family.

The makeup-removing or cleaning compositions serve to eliminate all spots or stains present on the surface of the skin, which spots or stains are the result of make-up with a pigment base, of particles coming from the atmosphere, and of fats present either in the make-up products or arising from an excess of sebum.

Numerous compositions have already been proposed to bring about the removal of make-up from the face and the eyes; these compositions are mainly based on the use of surface-active agents.

The employment of a surface-active agent with good detergent qualities is indispensable in this type of composition in order to obtain a good elimination of those make-up products that are especially greasy, such as complexion bases, rouge, mascara, eye-liners, and the like.

In addition, these surface-active agents must offer as little irritation as possible in order to prevent certain feelings of discomfort on the part of the users when the composition comes into contact with the mucous membrane of the eye.

This quality is very important when the compositions are especially intended for the removal of make-up from the eyes, as in this case the possibility of contact with the mucuous membrane of the eye is especially great.

It is evident from these different considerations that a good surface-active agent usable in the makeup-removing compositions for the face and the eyes must irritate the mucuous membrane of the eye as little as possible, while offering at the same time good detergent action.

It has been ascertained that such a result can be obtained when the synthetic surface-active agents are combined with an extract of sarsaparilla, the latter having the effect of reducing their aggressiveness while at the same time strengthening the detergent power.

The use of a sarsaparilla extract in the makeup-removing compositions according to the invention makes possible the obtainment of an excellent correspondence between the detergency and the ocular harmlessness, a development that could not be achieved till the present time with most of the synthetic surface-active agents when used alone.

In addition, it has been ascertained that the presence of a sarsaparilla extract in the compositions makes possible the slowing up of the return of oiliness to skin considered to be oily.

The object of the present invention is a new industrial object in the form of a cosmetic composition for the removal of make-up from the face and the eyes, containing, in so far as the cleaning substance is concerned, the combination of a synthetic surface-active agent and an extract of sarsaparilla (*Smilax Species*).

The synthetic surface-active agent of the compositions according to the invention can be selected from among a large number of substances, such as (i) the alkyl or hydroxyalkyl polyglucosides, of which the alkyl radical has from $C_{11}$ to $C_{18}$ and of which the number of glucoside units lies between 5 and 25, the alkyl radicals deriving preferably from such alkanols as dodecanol, tetradecanol, hexadecanol, or from mixtures of these alcohols and the hydroxyalkyl radicals deriving preferably from α-diols such as dodecanediol-1,2, tetradecanediol-1,2, hexadecanediol-1,2 or from mixtures of these diols.

As a representative compound of this class one may call attention especially to alkyl polyglucoside having 5 glucoside units, the alkyl radical of which derives from dodecanoic alcohol;

(ii) sorbitan monolaurate polyoxyethylenated with 20 moles of ethylene oxide (a product sold by the ATLAS Company under the name of "TWEEN 20");

(iii) sorbitan monooleate polyoxyethylenated with 20 moles of ethylene oxide (a product sold by ATLAS under the name of "TWEEN 80");

(iv) the polyoxyethylenated alkyl carboxylates of α-methyl glucoside, the alkyl radicals of which, linear or branched, saturated or unsaturated, have from 12 to 22 carbon atoms, such as mono- and di-laurates, mono- and di-palmitates, mono- and di-stearates, and mono- and di-oleates of α-methyl glucoside, polyoxyethylenated with 10 to 30 moles of ethylene oxide;

As a representative compound of this class of surface active agents, attention is called particularly to the mixture of mono- and di-stearate of α-methyl glucoside polyoxyethylenated with 20 moles of ethylene oxide (a product sold by the AMERCHOL Company under the name of "Glucamate SSE-20");

(v) the polyoxyethylenated esters of fatty acids and of glycerol, the fatty acid radical of which, saturated or unsaturated, contains from 12 to 18 carbon atoms, such as polyoxyethylenated monooleate or monolaurate of glycerol, preferably the monolaurate of glycerol oxyethylenated with 20 moles of ethylene oxide (a product sold by the GOLDSCHMIDT Company under the name of "TAGAT L2"), (vi) the disodium salt of the lauroyl-cycloimidinium-1-ethoxyethanoic-1-ethanoic acid (a product sold by the MIRANOL Company under the commercial name of "MIRANOL C2M"), (vii) a mixture of sulfates of fatty alcohols, such as the product sold by the HENKEL Company under the name of "TEXAPON ASV"), (viii) polyglycerolated ether of an α-diol having the formula

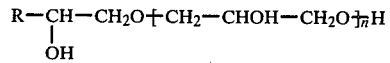

in which R represents a mixture of chains in $C_{10}$ and $C_{12}$ and n=3 to 4.

(ix) the polyglycerolated ethers having the formula:

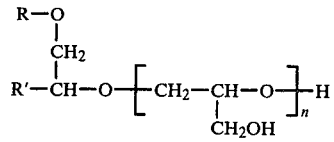

in which

R represents a linear saturated chain in $C_8$ and R' a linear saturated chain in $C_{16}$ and n is 10 or 12, (x) the amido-alkyl-betain of fatty acids having the formula:

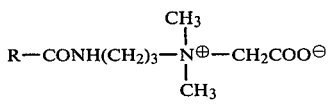

in which R represents $C_{11-17} H_{23-35}$, amphoteric surface-active agent, such as the one sold by the GOLDSCHMIDT Company under the name of "TEGO BETAIN L 7";

(xi) the imidazolinic derivatives of copra condensed with sodium lauryl ether sulfate, as, for example, the amphoteric surface-active agent sold by the REWO Company under the name of "STEINAPON AMCA";

and (xii) the glucoside ethers having the formula:

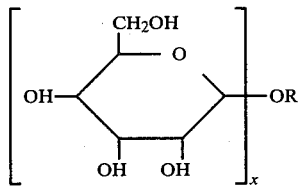

in which x represents from 1 to 5 and R is a 50/50 mixture of chains in $C_8$ and $C_{10}$, for example, the non-ionic surface-active agent sold by the ROHM & HAAS Company under the name of "TRITON CG 110".

Among the surface-active agents listed above, the preferred ones, according to the invention, are those of paragraphs (i) to (v) and (ix).

The surface-active agents are generally present in the makeup-removing compositions according to the invention at a concentration between 0.1 and 8% by weight, preferably, between 0.2 and 5%.

The sarsaparilla is a plant of the Liliaceae family and comprises several varieties according to their place of growth. Among the different varities of which the extracts can be used in the makeup-removing compositions in order to improve the relation between the detergent action and the harmless effect on the eyes, mention may be made in particular of: *Smilax medica, Smilax officinalis, Smilax regilii, Smilax glaberrina, Smilax aspera, Smilax aristolochiaefolia, Smilax papyraceae, Smilax febrifuga, Smilax ornata, Smilax saluberina, Smilax china*.

These different varities are encountered in various geographic zones, as Southern Europe, Central America, Brazil, the Equator, Mexico, etc.

The extracts of sarsaparilla are chiefly obtained from the roots of the plants. These extracts are characterized by the presence of saponosides of which the sapogenins are of steroidic structure.

The sarsaparilla extracts may be obtained by different processes, especially by maceration, digestion, decoction, infusion, or lixiviation.

All these methods are known; they are described in particular in the book entitled "L'OFFICINE" by Dorvault, Edition Vigot, 1978, pp. 569–573.

The sarsaparilla extracts obtained by these processes can take the form of liquid extracts, dry extracts, or soft extracts, but according to the invention one prefers to use dry extracts in the form of a powder having a characteristic odor.

Among the different processes of extraction, preference is given according to the invention either to aqueous extraction by one of the different processes listed above or to lixiviation with the help of a lower aliphatic alcohol having from 1 to 3 carbon atoms, such as methyl alcohol, ethyl alcohol, or isopropyl alcohol, the alcoholic degree of which lies between 20° and 100°, preferably between 65° and 75°, or with the help of a mixture of water and of methyl acetate or of acetone, this extraction by lixiviation being preferably carried out at room temperature.

One can use, in particular, the process described in French Pat. No. 1,520,375, which process consists of treating the pulverized sarsaparilla roots with ethyl (methyl or isopropyl) alcohol at about 70° and of condensing until a product of a pasty consistency has been obtained. The extract obtained is then retreated with boiling water, it is cooled, and one filters the insoluble part. The soluble portion in the water can then be concentrated to lead to liquid or dry extracts or it can be treated again in order to obtain purer and richer extracts in active substances.

The soluble portion can in fact be treated with the help of ammonium sulfate, and the precipitate obtained can be extracted with methanol or ethanol. After evaporation, a dry extract is obtained in the form of a powder which represents about 8 to 10% of the total weight of the roots treated initially.

In particular, one may use the process of decoction by allowing pulverized sarsaparilla roots to boil in water for 15 to 30 minutes and then to filter them.

The extract of sarsaparilla, expressed in dry matter, is present in the cosmetic compositions according to the invention at the rate of 0.1 to 10% by weight, preferably between 0.2 and 5% by weight, relative to the total weight of the composition.

The pH of the compositions is generally between 4 and 8.5, preferably between 6 and 8.

The compositions according to the invention may contain extracts from other plants, such as extracts of soapwort, ivy, horsetail, etc.

The cosmetic compositions according to the invention are preferably provided in the form of lotions, gels, milks, or creams.

When the compositions according to the invention are provided in the form of lotions, it is a question of liquid solutions obtained either with the sterile demineralized water or with floral water, such as rose water, cornflower water, camomile water or their mixtures.

These compositions preferably contain a preservative in a proportion between 0.002% and 0.3%, preferably between 0.02 and 0.2%, by weight relative to the total weight of the composition.

This preservative agent can be any one of the compounds generally used to prevent all bacterial contamination, during storage, of the compositions after they have been used for the first time.

Among the preservative agents one may list the following in a non-restrictive way: the esters of parahydroxybenzoic acid, such as the ethyl and propyl esters, merthiolate (sodium ethylmercurothiosalicylate), dihydrochloride or diacetate, but preferably the diglucamate of chlorhexihidine, the nitrate, borate or acetate of phenyl mercury, the benzylalkylammonium chlorides, such as myristyl-cetyldimethylbenzylammonium chloride, a mixture consisting of 30% of sodium benzoate and of 70% of monochloracetamide as well as certain other compounds of the quaternary ammonium type, like those known under the commercial names of "CETAVLON", "DOMIPHEN", and "DIOMETAN".

In order to maintain the pH in the zone indicated above, these compositions can also contain buffer mixtures, as, for example, a phosphate buffer (dipotassium hydrogen phosphate/potassium dihydrogen phosphate), a citrate buffer (sodium citrate—citric acid), a lactate buffer (sodium lactate—lactic acid), etc.

These compositions in the form of lotions can also contain a moistening agent such as hexyleneglycol or polyethylene glycol, a softening agent, and a thickening agent.

When the compositions according to the invention are makeup-removing milks or creams, these preferably take the form of emulsions of the oil-in-water type, the water phase constituting the continuous phase and the oil phase, the dispersed phase of the emulsion.

In these compositions in the form of emulsions, the water phase corresponds to about 30 to 95% by weight and the oil phase, to about 5 to 70% by weight relative to the total weight of the emulsion.

For the oil phase one can employ a great variety of products, such hydrocarbon oils, for example, paraffin oil, purcellin oil, perhydrosqualene and solutions of microcrystalline wax in the oils; animal and vegetable oils, such as sunflower oil, sweet almond oil, avocado oil, callophylum oil, lanolin, olive oil; mineral oils, of which the initial distillation point at atmospheric pressure is about 250° C. and the final point about 410° C.; saturated esters, such as isopropyl palmitate, alkyl myristates, such as those of isopropyl, of butyl, and of cetyl, hexadecyl stearate, ethyl palmitate, the triglycerides of octanoic and decanoic acids, and cetyl ricinoleate.

These emulsions for makeup removal can also contain diverse ingredients, as, for example, the preservative agents listed above for the lotions, antioxidants, amino acids as lysine or arginine, as well as perfumes.

Several examples of makeup-removing compositions according to the invention will now be given as an illustration for the better understanding of the invention.

EXAMPLE 1

One prepares a makeup-removing lotion for the eyes by means of a mixture of the following ingredients:

| Surface-active agent (Glucamate SSE-20) | 1 | g |
| --- | --- | --- |
| Dry extract of sarsaparilla | 0.5 | g |
| Hexylene glycol | 1 | g |
| Potassium dihydrogen phosphate | 0.102 | g |
| Potassium hydrogen phosphate . 3H$_2$O | 0.394 | g |
| Chlorhexidine dihydrochloride | 0.08 | g |
| Sodium benzoate | 0.03 | g |
| Monochloracetamide | 0.07 | g |
| Sterile demineralized water q.s.p. | 100 | g |

This composition used for the removal of makeup from the eyes makes possible a good elimination of the fatty pigments and substances without causing ocular trouble when the composition comes into contact with the eyes.

EXAMPLE 2

One prepares a makeup-removing milk by means of a mixture of the following ingredients according to the invention:

| Petrolatum oil | 10 | g |
| --- | --- | --- |
| Isopropyl palmitate | 5 | g |
| Dry extract of sarsaparilla | 1 | g |
| Surface-active agent (TWEEN 20) | 2 | g |
| Stearic acid | 1.4 | g |
| Triethanolamine | 0.7 | g |
| Carbopol 940 (carboxylic polymer sold by the GOODRICH Company) | 0.6 | g |
| Lysine | 0.5 | g |
| Propyl p-hydroxybenzoate | 0.1 | g |
| Sterile demineralized water q.s.p. | 100 | g |

EXAMPLE 3

One prepares a makeup-removing milk according to the invention by making a mixture of the following ingredients:

| Sunflower oil | 7 | g |
| --- | --- | --- |
| Mineral Oil | 5 | g |
| Isopropyl myristate | 3 | g |
| Dry extract of sarsaparilla | 2 | g |
| Surface active agent (Tagat L 2) | 1.5 | g |
| Stearic acid | 1.4 | g |
| Triethanolamine | 0.7 | g |
| Carbopol 940 | 0.5 | g |
| Arginine | 0.4 | g |
| Antioxidant agent (mixture of butylhydroxyanisole and of butylhydroxytoluene) | 0.007 | g |
| Perfume | 0.05 | g |
| Methyl p-hydroxybenzoate | 0.05 | g |
| Propyl p-hydroxybenzoate | 0.05 | g |
| Sterile demineralized water q.s.p. | 100 | g |

What is claimed is:

1. A makeup removal composition comprising in an aqueous carrier a cleansing amount of a surface active agent selected from the group consisting of (1) alkyl or hydroxyalkyl polyglucoside wherein the alkyl moiety has 11–18 carbon atoms and which has 5–25 glucoside units, (2) sorbitan monolaurate polyoxyethylenated with 20 moles of ethylene oxide, (3) sorbitan monooleate polyoxyethylenated with 20 moles of ethylene oxide, (4) polyoxyethylenated alkyl or alkenyl carboxylate of α-methyl glucoside wherein the alkyl or alkenyl moiety has 12–22 carbon atoms, (5) polyoxyethylenated ester of a fatty acid and glycerol wherein the fatty acid contains 12–18 carbon atoms, (6) the disodium salt of lauroyl-cycloimidinium1-ethoxyethanoic-1-ethanoic acid, (7) a mixture of fatty alcohol sulfates, (8) polyglycerolated ether of an α-diol having the formula

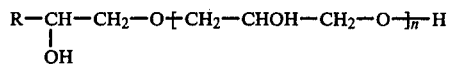

wherein R represents a mixture of $C_{10}$ and $C_{12}$, and n is 3 or 4, (9) polyglycerolated ether having the formula

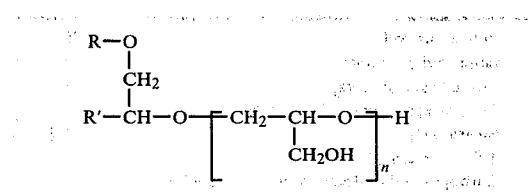

wherein R is linear saturated $C_8$, R' is linear saturated $C_{16}$ and n is 10 or 12,

(10) amino-alkyl-betain of fatty acids having the formula

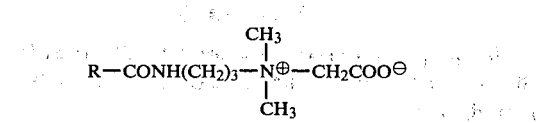

wherein R is $C_{11-17}H_{23-25}$,

(11) the imidazolinic derivative of copra condensed with sodium lauryl ether sulfate, and

(12) a glucoside ether having the formula

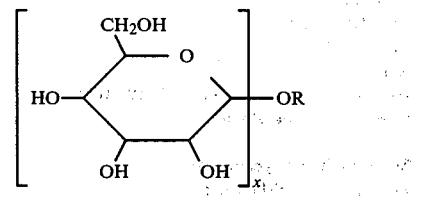

wherein x is 1–5 and R is 50/50 mixture of $C_8$ and $C_{10}$, and an effective amount of an extract of sarsaparilla (Smilax Species).

2. The composition of claim 1 wherein said surface active agent is present in an amount from 0.1–8 percent by weight based on the total weight of said composition and said extract of sarsaparilla is present in an amount, expressed on a dry basis, from 0.1–10 percent by weight of said composition.

3. The composition of claim 1 which includes a preservative in an amount between 0.002 and 0.3 percent by weight based on the total weight of the composition.

4. The composition of claim 10 having a pH ranging from 4 to 8.5.

5. A makeup removal composition in the form of an oil-in-water emulsion wherein the water phase is about 30–95 weight percent based on the total weight of the emulsion and the oil phase is about 5 to 70 weight percent based on the total weight of the emulsion, said composition including an extract of sarsaparilla (Smilax Species) present in an amount, expressed on a dry basis, from 0.1 to 10 percent by weight of said composition and a synthetic surface active agent present in an amount from 0.1–8 percent by weight of said composition, said surface active agent being selected from the group consisting of (1) alkyl or hydroxyalkyl polyglucoside wherein the alkyl moiety has 11–18 carbon atoms and which has 5–25 glucoside units, (2) sorbitan monolaurate polyoxyethylenated with 20 moles of ethylene oxide, (3) sorbitan monooleate polyoxyethylenated with 20 moles of ethylene oxide, (4) polyoxyethylenated alkyl or alkenyl carboxylate of α-methyl glucoside wherein the alkyl or alkenyl moiety has 12–22 carbon atoms, (5) polyoxyethylenated ester of a fatty acid and glycerol wherein the fatty acid contains 12–18 carbon atoms, (6) the disodium salt of lauroyl-cycloimidinium-1-ethoxyethanoic-1-ethanoic acid, (7) a mixture of fatty alcohol sulfates, (8) polyglycerolated ether of an α-diol having the formula

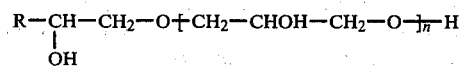

wherein R represents a mixture of $C_{10}$ and $C_{12}$, and n is 3 or 4, (9) polyglycerolated ether having the formula

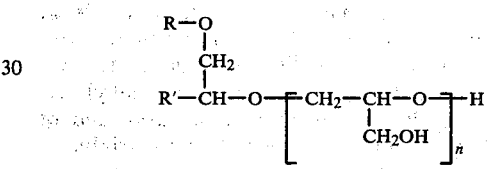

wherein R is linear saturated $C_8$, R' is linear saturated $C_{16}$ and n is 10 or 12,

(10) amino-alkyl-betain of fatty acids having the formula

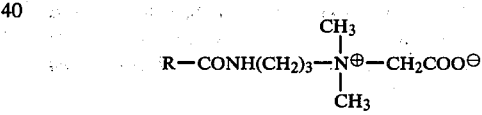

wherein R is $C_{11-17}H_{23-25}$,

(11) the imidazolinic derivative of copra condensed with sodium lauryl ether sulfate, and

(12) a glucoside ether having the formula

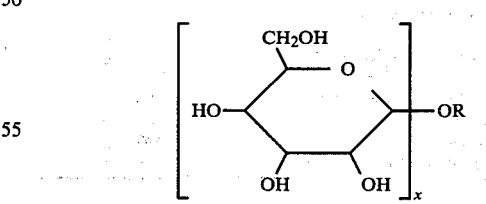

wherein x is 1–5 and R is 50/50 mixture of $C_8$ and $C_{10}$.

* * * * *